United States Patent
Vanga, Jr. et al.

(10) Patent No.: US 12,011,521 B2
(45) Date of Patent: Jun. 18, 2024

(54) AIR STERILIZING ELEVATOR CAB AND METHODS

(71) Applicant: Sterilyft LLC, Bronx, NY (US)

(72) Inventors: Carlos Vanga, Jr., Baldwin Place, NY (US); Nick Gretsuk, Holbrook, NY (US)

(73) Assignee: Sterilyft LLC, Bronx, NY (US)

( * ) Notice: Subject to any disclaimer, the term of this patent is extended or adjusted under 35 U.S.C. 154(b) by 0 days.

(21) Appl. No.: 17/343,604

(22) Filed: Jun. 9, 2021

(65) Prior Publication Data

US 2022/0008604 A1    Jan. 13, 2022

Related U.S. Application Data

(60) Provisional application No. 63/051,183, filed on Jul. 13, 2020.

(51) Int. Cl.
*A61L 9/20* (2006.01)
*B66B 11/02* (2006.01)

(52) U.S. Cl.
CPC .............. *A61L 9/20* (2013.01); *B66B 11/024* (2013.01); *A61L 2209/12* (2013.01); *A61L 2209/14* (2013.01); *A61L 2209/16* (2013.01)

(58) Field of Classification Search
CPC .... A61L 9/20; A61L 2209/12; A61L 2209/14; A61L 2209/16; B66B 11/024
See application file for complete search history.

(56) References Cited

U.S. PATENT DOCUMENTS

| | | | |
|---|---|---|---|
| 3,576,593 A | 4/1971 | Cicirello | |
| 4,255,383 A | 3/1981 | Schenck | |
| 5,074,894 A * | 12/1991 | Nelson | F24F 3/167 96/224 |
| 5,112,370 A | 5/1992 | Gazzano | |
| 5,330,722 A | 7/1994 | Pick et al. | |
| 7,407,633 B2 | 8/2008 | Potember et al. | |
| 7,498,004 B2 | 3/2009 | Saccomanno | |
| 7,692,172 B2 | 4/2010 | Leben | |
| 8,097,861 B2 | 1/2012 | Leben | |
| 8,211,208 B2 | 7/2012 | Chan et al. | |
| 8,519,361 B2 | 8/2013 | Leben | |
| 8,680,496 B2 | 3/2014 | Leben | |

(Continued)

FOREIGN PATENT DOCUMENTS

| | | | | |
|---|---|---|---|---|
| CN | 212151259 U | * | 12/2020 | .............. B66B 11/02 |
| KR | 2020019338 | * | 2/2020 | ........... A61L 2/0088 |
| WO | WO-2019024145 A1 | * | 2/2019 | ................ A61L 9/20 |

OTHER PUBLICATIONS

English translation of CN-212151259-U of (Year: 2020).*

*Primary Examiner* — Regina M Yoo
(74) *Attorney, Agent, or Firm* — Weber Rosselli & Cannon LLP

(57) ABSTRACT

An elevator cab and method of sterilizing the air of an elevator comprising, a plenum configured to fluidly connect to an interior of the elevator cab, at least one intake formed in the side walls of the elevator cab and in fluid communication with the plenum, a fan configured to draw air from the elevator cab via the intake duct and the plenum, and a kill box, including a source of ultraviolet C (UVC) light, and configured to receive air via the fan, wherein the UVC light is configured to sterilize air removed from the elevator cab.

6 Claims, 8 Drawing Sheets

(56) References Cited

U.S. PATENT DOCUMENTS

| | | | |
|---|---|---|---|
| 9,393,338 B2 | 7/2016 | Livchak et al. | |
| 9,457,120 B2 | 10/2016 | Matsui | |
| 9,696,049 B2 | 7/2017 | Metteer | |
| 10,548,764 B2 * | 2/2020 | Alzeer | A61L 2/10 |
| 2004/0041564 A1 | 3/2004 | Brown | |
| 2006/0070823 A1 | 4/2006 | Huang et al. | |
| 2021/0299291 A1 * | 9/2021 | Mullen | H05K 1/038 |
| 2021/0354958 A1 * | 11/2021 | Mandy | F24F 1/0073 |
| 2021/0386900 A1 * | 12/2021 | Blum | A61L 9/145 |

* cited by examiner

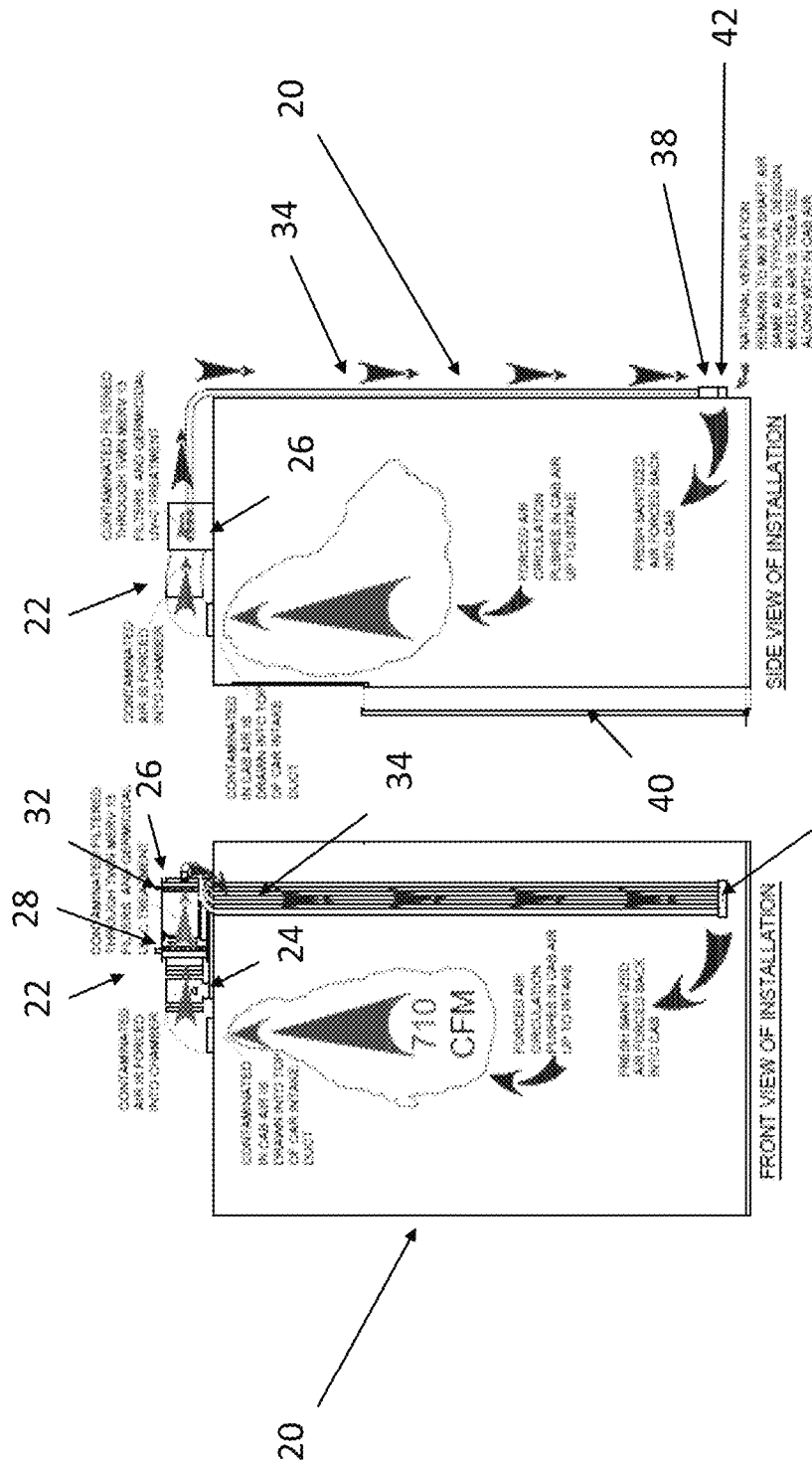

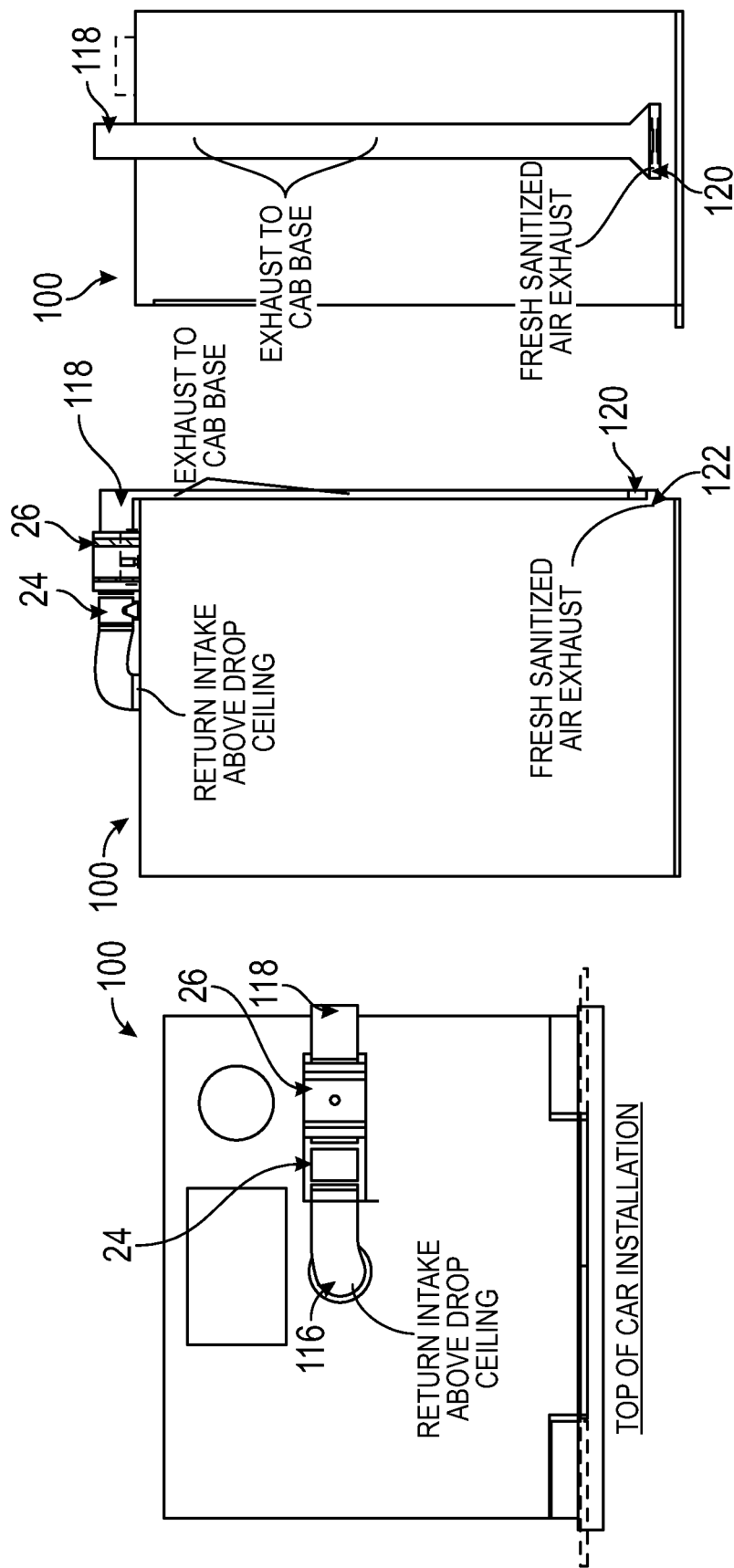

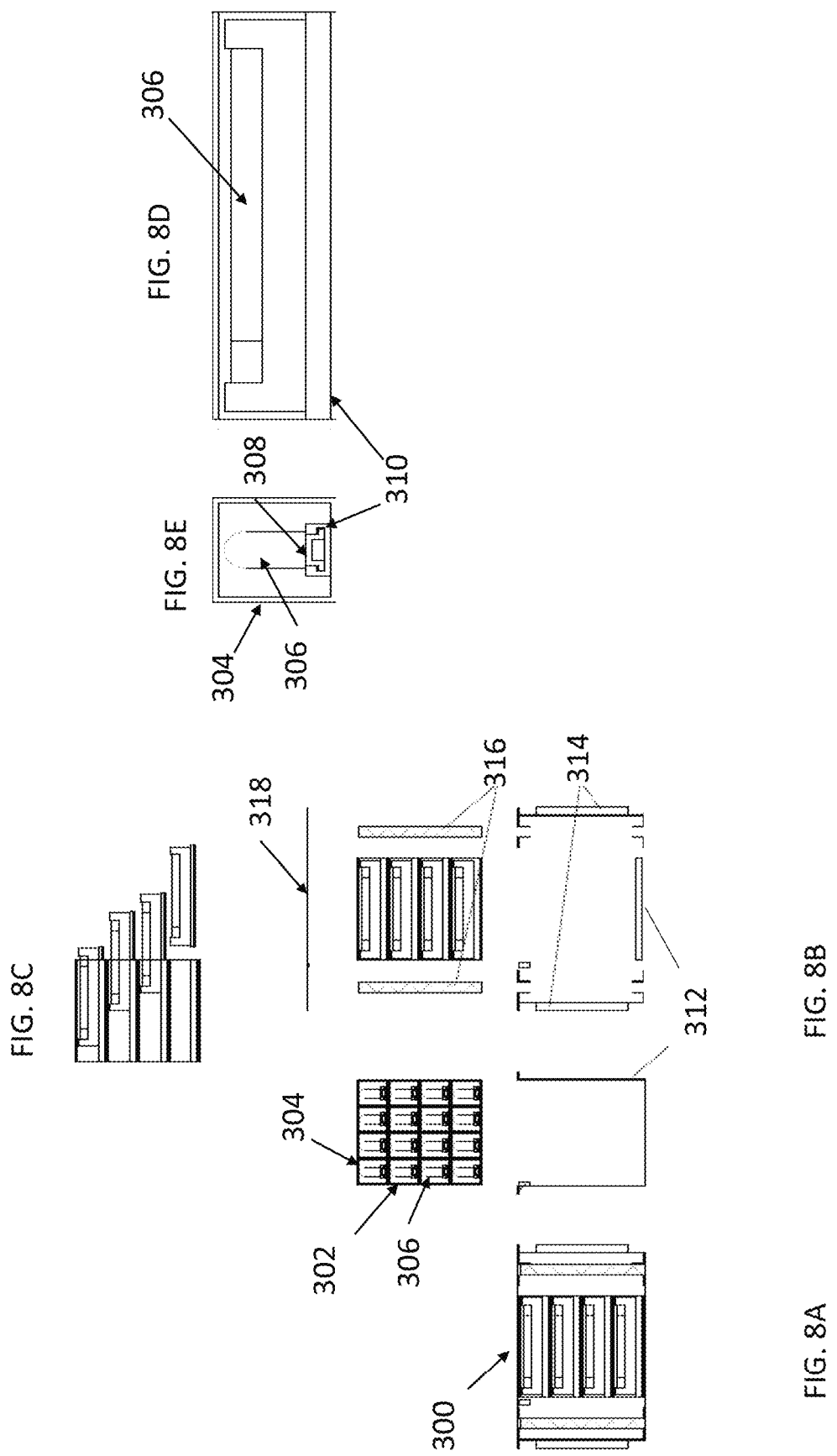

AIR STERILIZING ELEVATOR CAB AND METHODS

TECHNICAL FIELD

The instant disclosure relates to an air sterilization system, an elevator having the air sterilization system and methods of sterilizing elevator air to be substantially pathogen and virus free.

BACKGROUND

Generally, an elevator which moves in a vertical direction of a building is installed in a multistory building in which it is difficult to go up and down the stairs or a building having a large floating population such as an apartment, a hospital, office building or a department store to meet the convenience of passengers (users) of the building.

A door is installed in the elevator and the passengers get into the elevator through the door. Since the elevator moves up and down while the door is closed, an inner space of the elevator which is used by many passengers including those that may be sick with or simply carriers of a variety of pathogens including viruses such as the recently identified COVID-19 virus. In addition, the elevator may transport cargo contaminated with various viruses, bacteria, fine dust particles, mold, and the like. Accordingly, when the passengers get into the elevator having a contaminated inner space, these pathogens can be transmitted to the air in the elevator, the pathogens may enter a body through respiratory organs or may be stuck to clothes or a body. Particularly, older, infirm or persons with co-morbidities such as respiratory and pulmonary issues, as well as children and healthy adults can struggle and as recently seen require hospitalization or even suffer death because of these airborne contaminants.

Some approaches to these issues have been attempted, however, the most known solution has multiple short comings. FIG. 1A depicts a typical elevator cab 10. The elevator cab 10 includes an air handler 12 that includes a fan to force air from the elevator shaft into the elevator cab 10. Because the elevator shaft is not a particularly clean space, the air handler 12 may include one or more filters (not shown) to remove particles from the shaft air before forcing the air into the elevator cab 10.

However, as can be seen with reference to FIGS. 1A and 1B, the forcing of air into the elevator cab 10 from the top of the elevator cab 10 results in the forcing of air past the occupants in the direction of the floor, this necessarily results in the air currents eddying back towards the top of the elevator cab. There is nowhere for the air to go as it is continually forced into the elevator cab 10, thus the air circulates within the elevator cab 10. The filtered air mixes with the air that is exhaled from the passengers and thus becomes contaminated with any pathogens that the passenger may be expelling. Further, there is no further filtering of this air.

A small vent 14, located near the floor is the only return of the air from the elevator cab 10 to the shaft from which the air was originally drawn. However, this vent only prevents over pressurization of the elevator cab 10 and is primarily only effective at allowing air to flow out of the elevator cab 10 when the elevator cab is at rest. Further, because of this pressurization of the elevator cab 10, every time the doors 16 open, the air in the elevator cab 10, which is a mixing of the filtered air from the air handler 12 and the air expelled from passengers is ejected out of the elevator cab 10 and into any vestibule or landing opposite the doors 16. The result is an actual increase in the potential for contamination of not just the elevator cab 10, but an entire building as pathogens are potentially deposited with each stop where a passenger enters or exits the elevator cab 10.

Still further, while filtration methods can remove some of the particles from the air prior to entry into the elevator cab 10, they too have shortcomings. In view of the presence of heat and humidity, the filtration systems while they remove the pathogens from the air does not kill the pathogens but rather provide a rich environment for the pathogens to replicate and spread within the filtration medium. This causes issues with both the personnel maintaining the air filtration systems as well as presenting a potential source of re-contamination of the very elevator cab 10 whose air was to be cleaned. Accordingly, improvements are desired to improve the quality of the air in the elevators.

SUMMARY

One aspect of the disclosure is directed to an elevator cab including: at least one intake duct formed in a ceiling of the elevator cab; a fan configured to draw air from the elevator cab via the intake duct; at least one filter configured to filter the air drawn from the elevator cab by the fan; and a kill box, including a source of ultraviolet-C (UVC) light, and configured to receive air via the fan, where the UVC light is configured to sterilize air removed from the elevator cab.

Implementations of this aspect of the disclosure may include one or more of the following features. The elevator cab where an exhaust side of the kill box is configured to exhaust sterilized air having passed through the kill box into an elevator shaft. The elevator cab further including an exhaust duct, the exhaust duct receiving sterilized air from the kill box and directing the sterilized air to an exhaust opening formed proximate a floor of the elevator cab. The elevator cab where the kill box includes a first filter positioned between the fan and the UVC light, and a second filter positioned between the UVC light and an outlet of the kill box. The elevator cab where a flow of elevator cab air through the kill box is slowed by the at least one filter, such that pathogens in the elevator air sterilized. The elevator cab where the fan, UVC light, and at least one filter are configured to reduce volatile organic compounds in the elevator air by about 32% or more. The elevator cab where the fan, UVC light, and at least one filter are configured to reduce particles less than 10 microns in the elevator air by about 95%. The elevator cab where the fan, UVC light, and at least one filter are configured to reduce particles less than 2.5 microns in the elevator air by about 95%. The elevator cab where the fan, UVC light, and at least one filter are configured to reduce particles less than 1 micron in the elevator air by about 97%. The elevator cab where the fan, UVC light, and at least one filter are configured to reduce particles less than 0.3 microns in the elevator air by about 89%.

A further aspect of the disclosure is directed to a kill box including: a fan in fluid communication with an inlet duct; at least one ultraviolet-C (UVC) lamp; a first filter positioned between the fan and the UVC lamp, a second filter positioned between the UVC lamp and an outlet duct; and a substantially air-tight housing, configured to receive the first and second filters and the UVC lamp, where the filters ensure that air entering the substantially air-tight housing remains within the substantially airtight housing for sufficient time to ensure that particles in the air are sterilized.

Implementations of this aspect of the disclosure may include one or more of the following features. The kill box further including an electrical isolation switch in communication with a cover, where removal of the cover ensures that the UVC lamp cannot be energized. The kill box further including two UVC lamps. The kill box where the fan, UVC light, the first filter, and the second filter are configured to remove from air passing through the kill box about 95% of particles having a size of less than 10 microns. The kill box where the fan, UVC light, the first filter, and the second filter are configured to remove from air passing through the kill box about 95% of particles having a size of less than 2.5 microns. The kill box where the fan, UVC light, the first filter, and second filter are configured to remove from air passing through the kill box about 97% of particles having a size of less than 1 micron. The kill box where the fan, UVC light, the first filter and the second filter are configured to remove from the air passing through the kill box about 89% of particles having a size of less than 0.3 microns.

Yet a further aspect of the disclosure is directed to a room sterilization system including: a housing configured to receive at least one filter; an ultraviolet-C (UVC) lamp mounted in the housing; fan configured to force air through the housing and the at least one filter, where the air is exposed to UVC light from the UVC lamp; an exhaust duct configured to receive the air from the housing; a register in fluid communication with the exhaust duct and configured to expel air into the room; a plurality of air inlets in fluid communication with the room; a plurality of chase ducts in fluid communication with the air inlets and the fan, such that suction created by the fan draws air from the room through the air inlets and chase ducts and into an inlet side of the fan; where the at least one filter is configured to ensure the air drawn from the room remains in the housing for sufficient time that any pathogens in the air are sterilized.

Implementations of this aspect of the disclosure may include one or more of the following features. The room sterilization system where the fan, UVC lamp, and at least on filters are configured to remove at least 90% of all viral, bacteria, and mold for the air in the room in about 2 minutes or less. The room sterilization system where the fan, UVC lamp, and at least on filters are configured to remove at least 99% of all viral, bacteria, and mold for the air in the room in about 10 minutes or less.

BRIEF DESCRIPTION OF THE DRAWINGS

These and/or other aspects and advantages of the exemplary embodiments of the invention will become apparent and more readily appreciated from the following description of the embodiments, taken in conjunction with the accompanying drawings, of which:

FIG. 2A depicts a front view of an elevator cab and a sterilization system in accordance with the disclosure;

FIG. 2B depicts a side view of an elevator cab and a sterilization system in accordance with the disclosure;

FIG. 5A depicts a top view of an elevator cab incorporating an air sterilization system in accordance with the disclosure;

FIG. 5B depicts a rear view of an elevator cab incorporating an air sterilization system in accordance with the disclosure;

FIG. 5C depicts a side view of an elevator cab incorporating an air sterilization system in accordance with the disclosure;

FIG. 8A is a kill box in accordance with the disclosure;

FIG. 8B is an exploded view of the kill box of FIG. 8A;

FIG. 8C is a side perspective view of a diffuser of the kill box of FIG. 8A, showing the removability of the lamps;

FIG. 8D is a side view of a removable lamp in accordance with the disclosure; and FIG. 8E is an end view of the removable lamp of FIG. 8D.

DETAILED DESCRIPTION OF THE EMBODIMENTS

Figures 1A, 1B:
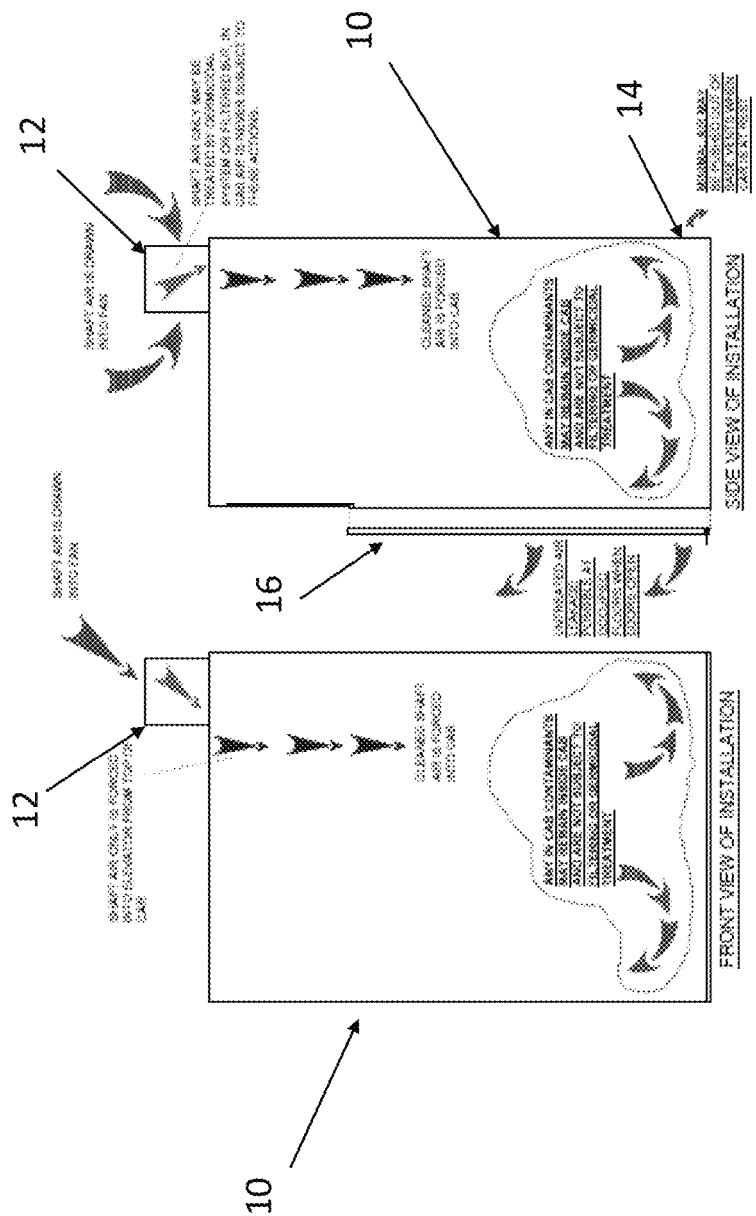
FIG. 1A depicts a front view of a known elevator and air handler system.
FIG. 1B depicts a side view of a known elevator and air handler system.

Reference will now be made in detail to exemplary embodiments of the disclosure, examples of which are illustrated in the accompanying drawings. The embodiments are described below to explain the disclosure by referring to the figures.

The effects of ultraviolet-C (UVC) light on pathogens such as viruses, bacteria, mold, and others have been researched and several studies have been conducted on use of UVC lighting to clean water, air, and solid surfaces. In the UV spectrum which includes UVA, UVB and UVC, UVC light is the portion of the spectrum having a wavelength between 100 and 380 nm (nanometers). As this portion of the UV spectrum does not naturally reach Earth's surface from the sun (only UVA and UVB penetrate the atmosphere), UVC's effects on pathogens such as viruses and bacteria is e profound and quite destructive. Testing within the UVC band found that the maximum "germicidal" range was between 200 to 300 nm (curve of effectiveness in molecular destruction of the DNA bond beginning at 200 nm, ending at 300 nm respectively). Further it was determined that UVC has a peak performance in effectiveness in the inactivating (killing) of pathogens such bacteria and virus at about 254 nm. Importantly for the context facing the world now of this writing, tests performed on H1N1, SARS, and MRSA were all successful in killing these prior viruses with UVC radiation. The current, t "Corona virus," COVID-19 is like both SARS and MERS (previous Corona viruses). It is believed that UVC is similarly effective in killing COVID-19.

While UVC is effective in killing pathogens such as bacteria and viruses, exposure to UVC does not kill these pathogens instantly. Owing to a hardened exterior, it has been observed that effective killing of airborne viruses (e.g., nucleic acid destruction of viral DNA) requires some period, and the longer the exposure the greater likelihood of achieving complete destruction of the viruses in any given sample. Despite the increased length of time studies suggest that a true "sterilization" of all particles (i.e., 100% destruction) would be impracticable in most day-to-day situations. In part this is due to processes such as photoreactivation and base excision where a cell repairs destroyed DNA damaged by UV light. Nonetheless, elimination of substantially all viruses and other pathogens within a confined space such as an elevator substantially reduces the risk of infection. When paired with other personal protection methods, including the wearing of a mask, hand washing, and refraining from touching one's face, it is believed that the systems and methods of the instant disclosure substantially eliminate the likelihood of being passively infected by others during an elevator ride. As will be appreciated, no system will eliminate the risk of an unmasked infected rider openly sneezing in an elevator infecting the current passengers. But the systems and methods described herein will substantially reduce the risk for subsequent riders of the very same elevator.

FIGS. 2A and 2B depict an elevator cab 20 incorporating a sterilizing air handler 22 in accordance with the disclosure. The sterilizing air handler 22 draws air from within the elevator cab 20. A fan 24 creates a suction that in one embodiment can create a volumetric flow of about 700 ft$^3$/min of air from the elevator cab 10 and into a kill box 26. Those of skill in the art will recognize that the volumetric flow rate can be greater or lower than 700 ft$^3$/min depending on the size of the elevator. A smaller elevator may be effectively treated at a lower volumetric flow rate, and the volumetric flow rate may be increased for a larger elevator cab 20. As will be described in greater detail below, one metric for assessment of the volumetric flow rate for a given space is the number of air changes per hour (ACH), which is in part a function of the volumetric flow rate of the fan 24 employed for a given space (e.g., an elevator cab).

Figure 3:
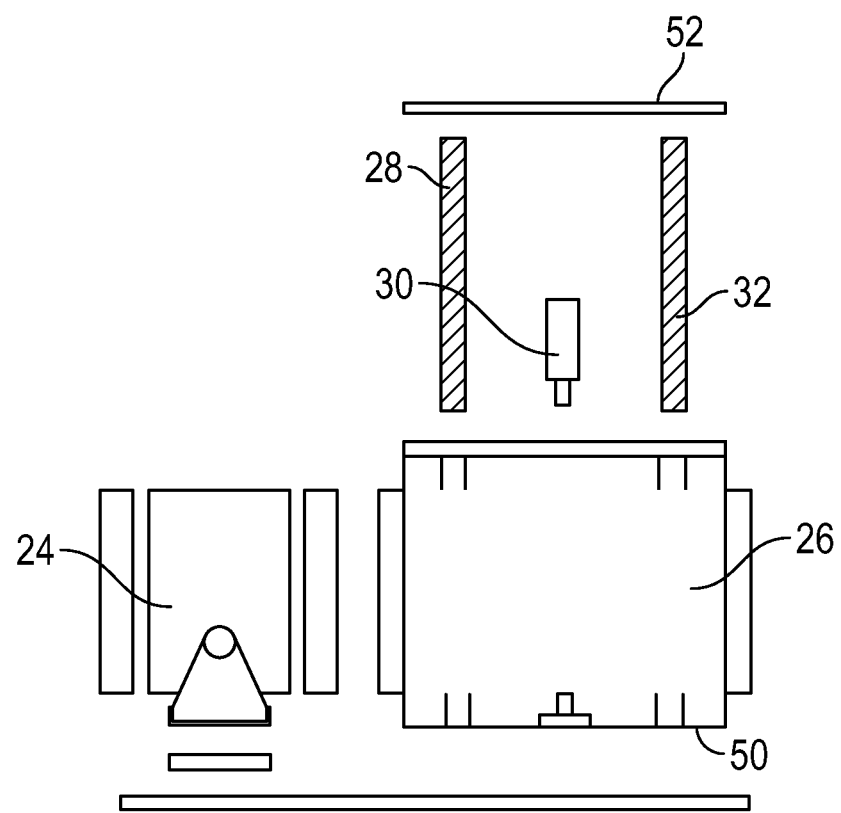
FIG. 3 depicts an air sterilization system in accordance with the disclosure.

The kill box 26 includes a pre-filter 28, a UVC lamp 30 and a post filter 32 (see FIG. 3). The combination of the pre-filter 28 and the post filter 32 act to slow the flow of air through the kill box 26. This slowing of the flow of air ensures that the air is trapped in the kill box 26 for a period of time sufficient to ensure that the air within the kill box 26 is exposed to the UVC emitted from the UVC lamp 30 for sufficient time to destroy any pathogens in the air and effectively sterilize the air. The UVC lamp 30 also ensures that any pathogens captured by either the pre-filter 28 and the post filter 32 are also destroyed preventing replication and spread of the pathogens within the kill box 26.

After passing through the post filter 32, the now sterilized air passes through a plurality of outlet ducts 34. The outlet ducts 34 extend along a wall, for example the back wall 36 of the elevator cab 20 and terminate at an exhaust manifold 38. The exhaust manifold 38 connects the outlet ducts 34 to the interior of the elevator cab 20 and is located near the floor of the elevator cab 20. The sterilized air exits from the exhaust manifold 38 and is forced into the elevator cab 20. The combination of the sterilized air being forced from the exhaust manifold 38 and the suction generated by the fan 24 works in combination to draw the sterilized air through the interior of elevator cab 20, past any passengers who might be in the elevator cab and towards the kill box 26, where the air can be continually sterilized.

As will be appreciated, by having fan 24 create a suction drawing sterilized air from the exhaust manifold 38, located near the floor level, in the direction of the ceiling any pathogens expelled by a passenger are drawn up and away from the passengers and towards the kill box 26 where they can be sterilized. Similarly, by creating a suction, upon opening of the doors 40 rather than having pressurized air being forced out of the elevator cab 20, the air in the elevator cab 20 generally remains in the elevator cab 20 and indeed, the fan 24 may draw air into the elevator cab 20 from the landing or vestibule at which the elevator cab 20 stops.

A vent 42 may also be formed in a wall (e.g., the back wall 36) connecting the elevator shaft to the interior of the elevator cab 20. A relatively small amount of air may be drawn into the elevator cab 20 via the vent 42.

FIG. 3 depicts an exploded view of the kill box 26 in accordance with the disclosure. As described above, the kill box 26 includes one or more UVC lamps 30 placed between the pre filter 28 and the post filter 32 within a housing 50. A cover 52 encloses the UVC lamps 30, the pre-filter 28 and the post filter 32 lamp(s) 30 and the filters 28, 32 in the housing.

As shown in FIG. 3, but also relevant to the embodiments of FIG. 2, the fan 24 is connected to an intake side of the kill box 26, though the fan 24 could also be connected to the exhaust side of the kill box 26 without departing from the scope of the disclosure. The fan 24 either draws or forces air through the pre-filter 28, through housing 50, and through the post filter 32. The filters 28 and 32 perform two primary tasks. First, and obviously they filter air that passes through them. This removes many particles from the air but may not remove viruses and other pathogens which may have a smaller average diameter than the pore size of the pre-filter filter 28. The second primary task of the filters 28, 32 is that they slow down the velocity of the air being forced or drawn into the kill box 26. This slowing down of the velocity of the air ensures that the air takes a longer time to pass through the housing 50 and extends the period of exposure to the UVC emitted from the UVC lamp 30. As noted above, the longer the air and more particularly the pathogens in the air are exposed to the UVC light, the greater likelihood that the air will be sterilized, and the pathogens rendered inert or at least not harmful.

The lamp 30 may for example be a PHILIPS® TUV TL mini T5 germicidal lamp however, other lamps may be used without departing from the scope of the disclosure. A plurality of lamps 30 may be connected in series to ensure that UVC emission occurs throughout the length of the housing 50. The lamps 30 may be connected electrically in parallel to prevent one failure from stopping the emission of UVC light. Further, a monitoring device may be incorporated into the housing to alert the operator of the elevator (e.g., building management) of such a failure of a lamp 30 so that remedial action can be undertaken. Still further, for some elevator designs it may be desirable employ two or more kill boxes 26 to increase the removal of contaminated air from the elevator.

Test 1

A comparative study of two elevators was undertaken over the course of a month to assess the effectiveness of the sterilizer system of FIG. 2 in improving the air quality within the elevator cab 20. The sterilizer system was installed in elevator cab 1 and elevator cab 2 was left unaltered to act as a control having a standard exhaust fan venting to the elevator shaft. Also installed in each elevator cab was an indoor air quality monitor capable of monitoring the following:

| | Recommended Exposure Limit | Agency | Elevator 1 | Elevator 2 |
|---|---|---|---|---|
| Temperature | 73-79 F. ° - Summer 68-75 F. ° - Winter | ASHRAE Std 62.1-2016 | w/n seasonal norm | w/n seasonal norm |
| Humidity | 30-65% Summer 20-65% Winter | ASHRAE Std 62.1-2016 | w/n seasonal norm | w/n seasonal norm |
| Particulate Matter less than 0.3 microns | None | N/A | 237 particles avg. | 2197 particles avg. |
| Particulate Matter less than 1 micron | None | N/A | 0.25 $\mu g/m^3$ | 9.86 0.25 $\mu g/m^3$ |
| Particulate Matter less than 2.5 microns | 35 $\mu g/m3$ (24 hours) | EPA (NAAQS) (24-hr mean) | 0.53 $\mu g/m^3$ | 12.6 $\mu g/m^3$ |
| Particulate Matter less than 10 microns | 50 $\mu g/m3$ | World Health Organization (WHO) (PM10) respirable particles (24-hr mean) | 0.59 $\mu g/m^3$ | 13.1 $\mu g/m^3$ |
| Carbon Dioxide (Calculated Equivalency) | Outdoors plus 700 | ASHRAE Std 62.1-2016 | Below recommended level | Below recommended level |
| Volatile Organic Compounds (VOCs) | 500 ug/m3 (300 ppb) | US Green Building Council | 422 ug/m3 | 284 ug/m3 |

In view of the above results, the air sterilization system of FIG. 2 as installed in an elevator cab was effective to reduce all particulate matter within the elevator cab and surprisingly also reduce the VOCs experienced in the elevator cab 20 by 32.7%. The use of the elevator cab sterilization system (described in connection with FIG. 2) resulted in 95.5 reduction particles less than 10 microns. It should be noted that 75% of viral carriers (e.g., sneeze, cough, or other expelled particulates are approximately 10 microns in size. 25% of viral carriers are in the range of 1-5 microns. Thus, the 95% reduction represents a significant reduction in the potential viral load of the air within the elevator cab 20. Similarly, particulate matter of less than 2.5 microns saw a reduction of 95.78%, particulate matter of less than 1 micron saw a 97.46% reduction and even particles less than 0.3 microns were reduced by 89.21%. Those of skill in the art will recognize that bacteria have an average size of about 0.4 microns, viruses range from 0.02 to 0.25 microns, and the COVID-19 corona virus has a size of about 0.125 microns. Accordingly, the elevator cab air sterilizing system depicted in FIG. 2 is effective in removing particulate matter down to the actual size of the pathogens in question. In addition, when coupled to with the UVC lamps 30, even particulate matter which might pass through both the pre-filter 28 and the post filter 32 is sterilized resulting in near complete (e.g., 99.9%) removal or sterilization of any pathogen load that might be found in the air of the elevator cab 20.

Figure 4C:
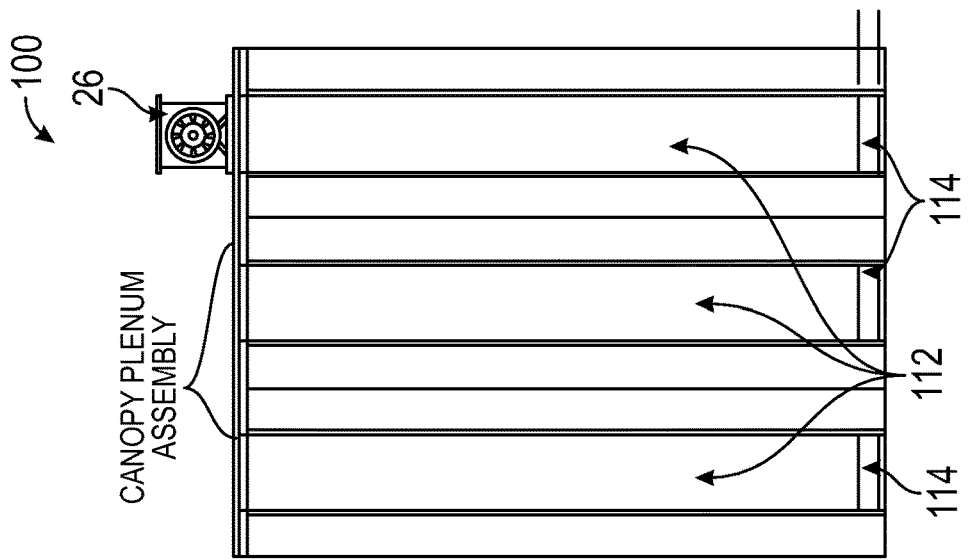
FIG. 4C depicts a rear view of an elevator cab incorporating an air sterilization system in accordance with the disclosure.
Figure 4B:
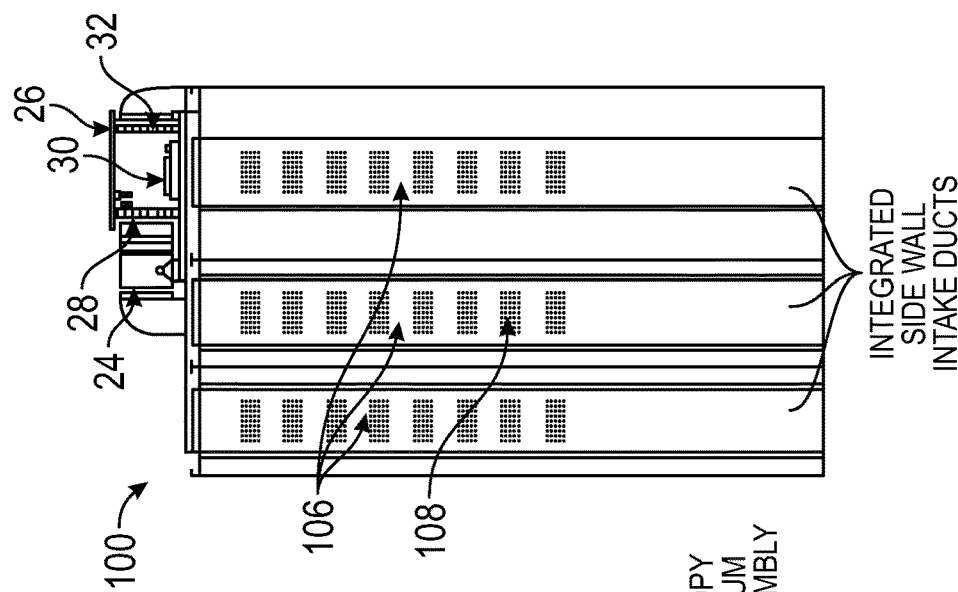
FIG. 4B depicts a side view of an elevator cab incorporating an air sterilization system in accordance with the disclosure.
Figure 4A:
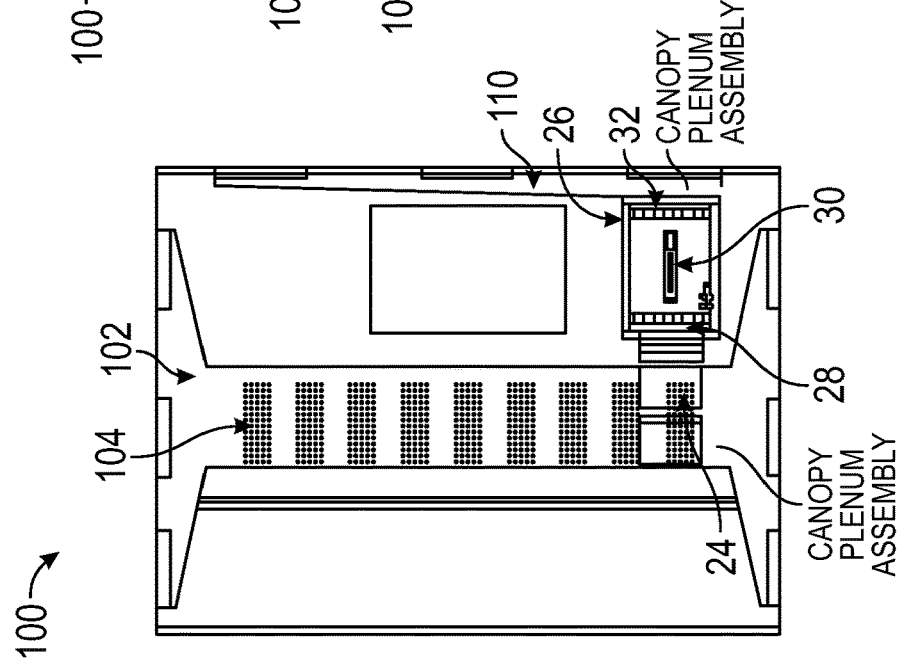
FIG. 4A depicts a top view of an elevator cab incorporating an air sterilization system in accordance with the disclosure.

FIGS. 4A-4C depict three views of an elevator cab 100 in accordance with the disclosure. FIG. 4A is a top view of an elevator cab 100. The fan 24 is connected to a kill box 26, as described above. An inlet side of the fan 24 connects to a plenum 102. The plenum 102 includes a series of openings 104 which enable air to flow from the interior of the elevator cab 100 and to the fan 24, where the air is forced into the pre-filter 28, past UVC lamp 30, and post filter 32 of the housing 50.

FIG. 4B depicts a side view of the elevator cab 100. The side walls 105 of the elevator cab 100 include intake ducts 106 which are connected to the interior of the elevator cab 100 via a series of openings 108, like openings 104 those formed in the plenum 102. The intake ducts 106 are in fluid communication with the plenum 102 and the fan 24. Accordingly, not only is the air from the interior of the elevator cab 100 drawn from above the heads of passengers within the elevator cab 100, but also directly from approximately the level of the heads and importantly the mouths and noses of the passengers. Further, the intake ducts 106 draw air from not just the top of the elevator cab 100, but also the sides of the elevator cab 100, thus increasing the likelihood that any expelled pathogens or particles are extracted from the elevator cab 100 without landing on another passenger The intake ducts 106 and the openings 108 connecting to the interior of the elevator cab 100 may start at approximately three feet above a floor of the elevator cab 100 and extend to proximate the ceiling of the elevator cab 100, where the intake ducts connects to the plenum 102.

FIG. 4C depicts a rear view of the elevator cab 100. The kill box 26, as seen in FIG. 4A connects to an exhaust plenum 110 on an exhaust side of housing 50 of the kill box 26. The exhaust plenum 110 connects to exhaust ducts 112 which extend the vertical length of the elevator cab 100. Openings 114, proximate the floor of the elevator cab 100 allow for the sanitized air flowing from the kill box 26 and through the exhaust plenum 110 to re-enter the elevator cab 100. By exhausting the sanitized air at the bottom of the elevator cab 100 and drawing air into the plenum 102 and intake ducts 106, a general airflow is created which limits the personal exposure of passengers of the elevator cab 100 to any un-sanitized air that is expelled by the riders. In this manner the elevator cab 100 of FIGS. 4A-4C provides for a highly efficient air flow, limiting exposure, and actively killing pathogens such as bacteria, mold, and viruses that can be found in the interior of the elevator cab. In particular, the elevator cab 100 is designed to actively move expelled pathogens from riders that become airborne and moves the air and the pathogens towards the kill box 26 where the air can be sanitized.

As compared to the current customary method of ventilating an elevator cab 100 from the elevator shaft, the embodiments of the disclosure draw the air from the elevator cab 100 itself. The kill box 26 eliminates the pathogens, and then this sanitized air is recirculated back into the elevator cab 100, ensuring the riders are always breathing substantially sanitized air, thus actively limiting the spread of pathogens from one passenger to the next via respiration.

A further aspect of the disclosure is directed to the placement of the kill box 26 such that it simply draws the air from the elevator cab 100 and exhausts the sanitized air to the elevator shaft. Rather than connect to an exhaust plenum 110 and exhaust ducts 112, the kill box 26 simply exhausts to the elevator shaft. Because the kill box 26 sanitizes the air removed from the elevator cab 100, there is little possibility for the pathogens to re-enter the elevator cab 100 or be expelled onto the individual floors. As with the prior embodiments, the pathogens are all, or substantially all, killed prior to exhausting to the elevator shaft. As air is drawn out the top of the elevator cab 100, the low pressure created in the elevator cab allows for fresh air, which has potentially already been sanitized to reenter the bottom of the elevator cab 100 via the vent (e.g., vent 42 FIG. 2B) as the elevator moves through the elevator shaft.

A further embodiment of the disclosure is depicted in FIGS. 5A-5C, which is a similar design to FIGS. 2A and 2B and designed to retrofit elevators which either have no recirculation system, as described above, or have a recirculation system, but which merely filter the air rather than employing a kill box 26. FIG. 5A depicts a top view of an elevator cab 100. An intake 116 fluidly connects to the interior of the elevator cab and enables a fan 24 to draw air from the elevator cab 100. The fan 24 exhausts to a kill box 26, as described above.

On the exhaust side of the kill box 10 an exhaust duct 118 connects to the manifold 20 on the exhaust side of the kill box 10. The exhaust duct 118 extends down a side 119 along substantially the entire height of the elevator cab 100 and exhausts via an exhaust opening 120 formed in the elevator cab 100 proximate the floor. The air entering the elevator cab 100 from the exhaust opening 120 is the recirculated air drawn in by the fan 24 via the intake 116 after having been sanitized in the kill box 26, described above. Though shown with a single exhaust duct 118 and exhaust opening 120, those of skill in the art will understand that multiple exhausts ducts 118 and exhaust openings 120 may be employed without departing from the scope of the instant disclosure. Further a small vent 122 prevents over pressurization of the elevator cab 100 and vents the sanitized air from the elevator cab 100 to the elevator shaft.

Again, in the embodiment of FIGS. 5A-5C the airflow is generally from the bottom of the elevator cab 100 to the top, which decreases the exposure of riders to pathogens that might be expelled by other riders. The size of the exhaust duct may be determined on an individual basis for an elevator considering the size of the elevator, space available for the retrofit, and other factors including the desired time for an air change of the elevator, the size of the fan 24, and building codes where relevant.

Figure 6:
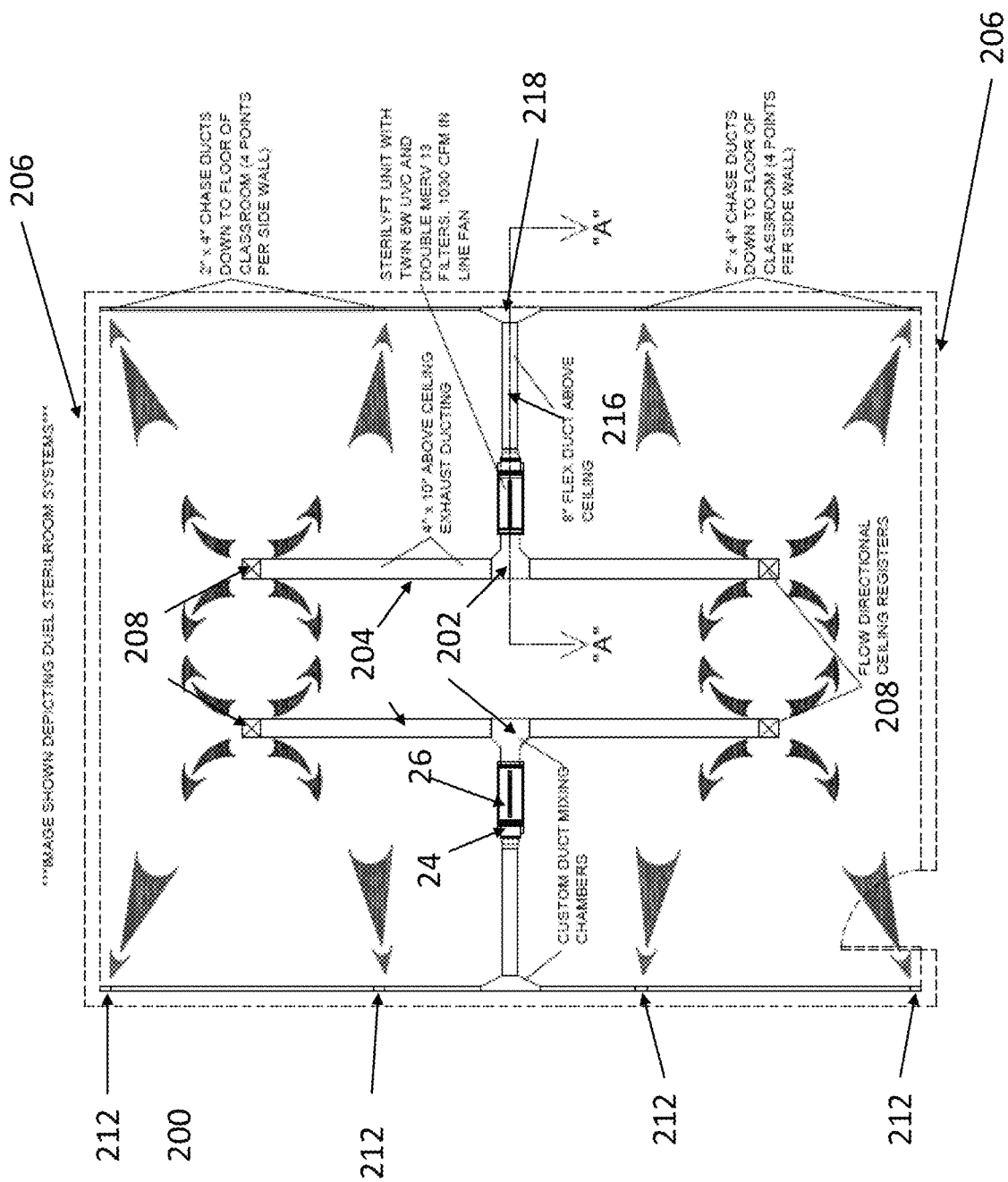
FIG. 6 depicts top view of a room sterilization system in accordance with the disclosure.

Yet a further aspect of the disclosure can be seen with respect to FIG. 6. Like elevator cabs, occupied spaces, where people will be in close proximity to one another can benefit from the disclosure. FIG. 6 depicts a room 200 in which an auxiliary germicidal treatment system is installed. Like the systems for the elevator cab, a fan 24 is employed in conjunction with a kill box 26. The kill box 26 is of substantially the same design as those for elevator cabs 20 and 100 and includes a pre-filter 28, one or more UVC lamps 30, a post filter 32 all contained within a housing 50 and having a cover 52. The fan 24 and kill box 26 may be mounted above a drop ceiling in a room, or directly to the ceiling such that it is visible within the room 200. On an outlet side of the kill box 26 is a first mixing chamber 202 from which extend a pair of exhaust ducts 204 extending at substantially right angles to a longitudinal axis (A-A) of the kill box 26.

Figure 7:
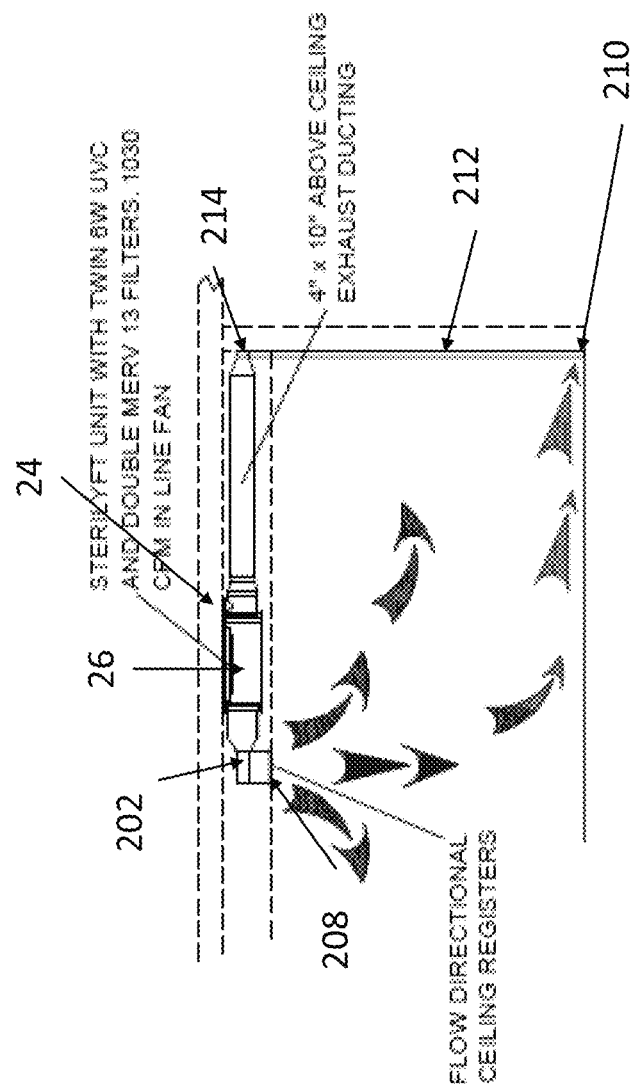
FIG. 7 is a side view of a room sterilization system in accordance with the disclosure.

The exhaust ducts 204 may be for example 4"×10" rectangular ducting (though other sizes may be employed depending on the size of the room and desired volumetric flow rate). The exhaust ducts 204 extend from approximately the center of the room 200 to between half and two-thirds of the distance to the walls 206 of the room 200. Each exhaust duct 204 terminates in a ceiling register 208. The ceiling register 208 diverts the flow of sanitized air from the kill box 26 in substantially all directions (e.g., 360 degrees about the ceiling register 208). In addition, the sanitized air is forced in the direction of the floor of the room 200. In the process of forcing the sterilized air in the direction of the floor any pathogens, particles or other undesirable matter that inhabits the air of the room is also forced towards the floor. Spaced at intervals (e.g., four per wall) and located near the floor are a number of intake openings 210. As depicted in FIG. 7, each intake opening 210 connects with a chase duct 212. The chase duct 212 may be for example a 2"×4" duct that extends from proximate the floor to a header 214 that connects all of the chase ducts 212 to an intake duct 216 via a mixing chamber 218. The intake duct 216 connects to the inlet side of the fan 24.

As will be appreciated the suction created by the fan 24 draws the air from the room 200 through the intake openings 210 and each chase duct 212 to the header 214 and the mixing chamber to the inlet duct 216 and into the kill box 26 where the air can be sterilized and filtered before being forced out the exhaust ducts 204 and the ceiling registers 208.

In some embodiments the header is a 2"×4" duct connecting each of the chase ducts 212. The intake duct 216 may be an 8" flexible duct or a 4"×10" rectangular duct. As will be appreciated, the sizes of all the ducts described in connection with this embodiment may be altered without departing from the scope of the disclosure. The sizes and the number of ducts may be based in part on the size of the room, the desired volumetric flow rate, and the desired number of complete air changes per hour for the system. As shown a chase duct 212 is located in each corner of the room as well as at two more evenly spaced locations along the wall of the room 200, though more or fewer chase ducts 212 may be deployed without departing from the scope of the disclosure. Thus, the system as depicted in FIG. 6 is completely scalable and may be customized to suit a given room size and dimensions.

As depicted in FIG. 6, two separate kill boxes 26 (and the attendant exhaust ducts 204, ceiling registers 208, intake openings 210, chase ducts 212, headers 214, and intake ducts 216 are depicted. These systems are separate but when used in combination enable greater volumetric flow through the kill boxes 26 and thus sanitization of the air in the room.

Table 2 describes the number air changes for a given size room that can be achieved by a single system, or a dual kill box system as depicted in FIG. 6. The Centers for Disease Control suggest that a room experience 6 air changes per hour (ACH) to promote a healthy environment. As can be seen below, the system depicted in FIG. 6, when employed in a room having approximately 10,000 ft$^3$ can achieve nearly double the number of ACH as recommend by the CDC.

TABLE 2

| Room air Volume (ft³) | 8000 | 9000 | 10000 | 12000 | 15000 | 20000 |
|---|---|---|---|---|---|---|
| Single Fan Flow Rate ft³/min | 946 | 946 | 946 | 946 | 946 | 946 |
| ft³/hr | 56760 | 56760 | 56760 | 56760 | 56760 | 56760 |
| Air Changes Per Hour | 7.095 | 6.301 | 5.676 | 4.73 | 3.784 | 2.838 |
| Two Fan Flow Rate ft³/min | 1892 | 1892 | 1892 | 1892 | 1892 | 1892 |
| ft³/hr | 113520 | 113520 | 113520 | 113520 | 113520 | 113520 |
| Air Changes Per Hour | 14.19 | 12.61 | 11.35 | 9.46 | 7.57 | 5.676 |

The room sterilization system depicted in FIGS. 6 and 7 enable installation of an air sterilization system without requiring extensive modification to existing ventilation systems. Further the room sterilization system can be employed in new construction as well. As noted above, the kill boxes 26 have a similar if not identical construction to those employed in elevator cab 20, though for a given room, the kill boxes 26 may be altered to enable more or less volumetric flow and greater or fewer ACH.

The system may be tied to thermostatic controls used in an existing heating ventilation and air-conditioning (HVAC) systems. Thus, the fans 24 can be cycled on during periods where the HVAC system is not engaged in heating or cooling of the air which, among other things assists in managing the electrical loads experienced in the building where these systems are employed.

Test 2

Utilizing the room air sterilization system of FIGS. 6 and 7, as described herein testing has been undertaken to confirm their efficacy in eliminating pathogens from the air. In particular samples of viruses, mold, and bacteria were released into the test chamber. A room was prepared having dimensions of 80" high, 70" wide, and 70" deep. Thus, the room had a volume of about 249.5 ft³. A kill box 26 with fan 24 was placed in the center of the room and an exhaust duct 204 connected to the outlet side of the kill box 26. During the testing microbial suspensions were aspirated into the chamber for 30 minutes. The fan 24 was turned on and samples were taken of the air at 0-, 1-, 2-, 3-, 4-, 5-, 10-, 15-, and 30-minute intervals. The process was repeated without the kill box 26 and fan 24 in the chamber to test for natural decay of the microbial suspensions in the air.

Summary of Results

| Organism Type | Virus | Mold | Bacteria |
|---|---|---|---|
| Temperature Min/Max | 20 C. - (68 F.) | 20 C. - (68 F.) | 20 C. - (68 F.) |
| Humidity Min/Max | 46% RH/53% RH | 46% RH/53% RH | 43% RH |
| Organism | Phi-X174 | A. niger | E. coli |
| 30 Minute Percent Reduction | 99.9% | 99.9% | 99.9% |

Further, while the 30-minute results are impressive, for each pathogen concentration was reduced by over 93% in just two minutes of operation. For example, the viral concentration was reduced by 95.8% in just two minutes of operation of the kill box 26 and achieved a 99.2% reduction in just 10 minutes of operation. The bacterial concentration was reduced by 96.8% in just two minutes of operation and achieved a 99.6% reduction in just 10 minutes. The mold concentration was reduced by 93.5% in just two minutes and achieved a 99.0% reduction in just four minutes of operation.

FIG. 8A illustrates a further embodiment of a kill box 300 in accordance with the disclosure. As shown in FIGS. 8B and 8E, the kill box 300 includes a diffuser 302 formed of a plurality of aluminum tubes 304. As shown each tube 304 is square, however, other shapes can be employed without departing from the scope of the disclosure. Each tube 304 is fitted with a lamp 306 emitting light in the UVC wavelength band, and preferably at about 254 nm. Each lamp 306 is mounted on a rail 308, that is received within a track 310 to slidably secure the lamp 306 in the tube 304. This rail 308 and track 310 arrangement enables easy sliding removal of a lamp 306 should it fail or need replacing. The track 310 may be sealed on the intake side of the kill box 300 to ensure that no air travels the length of the track 310 without exposure to the UVC light. The track 310 and rail 308 assembly also allows the kill box 300 to have all the lamps 306 removed, as shown in FIG. 8C and have both the lamps 306 and the interior surfaces of the kill box 300 cleaned.

The diffuser 302 is configured to be received within a housing 312. The housing 312 is airtight except for manifolds 314 formed on each end to receive intake and exhaust ducts as will be described in greater detail below. The housing 312 is also configured to receive two filters 316 (e.g., pre-filter and post filter), these may be for example HEPA filters or MERV filters. One filter 316 is placed on the intake side of the housing 312. The second filter 316 is placed on the exhaust side of the housing. A cover 318 seals the housing 312 and may be provided with an electrical interlock to remove power from the UVC lamps 306 in the event the cover 318 is removed from the housing 312. As depicted in FIG. 8B, the diffuser 302 is received in the housing 312 between the two filters 316.

With respect to the embodiment of FIG. 8B, the reduced volume of the individual tubes 304 as compared to the space between the filters 316 in the housing 312 further promotes the killing of pathogens by reducing the distance of travel the UVC light must make to reach the pathogens. Still further, the utilization of aluminum for the construction of the tubes 304, which is reflective of UVC light enables repeated exposure from not just the originally emitted light from the lamps 306, but also reflected UVC light. With each exposure to UVC light, both emitted and reflected, the total amount of UVC absorbed by the pathogens is increased and ultimately results in their destruction. Accordingly, whether employing the embodiment of FIG. 2 or the embodiment of FIG. 8A by double filtering the air and extending the time the air is exposed to the UVC lamp 306, substantially all the pathogens within the air can be killed and the air sterilized.

In one embodiment the diffuser 302 can be made of aluminum tubes 304 of nearly any length up to about 24 feet. Common lengths that might be employed including 10, 14, 24, 36, 48, and 60 inches. In one example the aluminum tubes 304 are approximately 2½"×2½" square tubing, but other dimensions may be utilized to meet the dimensions of the desired lamp 306. Though shown as a 4×4 matrix of aluminum tubes 304, the diffuser 302 need not be so limited, and instead may be configured of sufficient tubes to effectively sterilize the air at the appropriate speed. As will be appreciated larger elevators cabs may require longer and more aluminum tubes 304 than smaller elevators. The aluminum tubes 304 are preferably stacked and welded together, again to prevent any air from passing between the tubes 304 and not receiving sterilizing UVC light.

It will be understood that various modifications may be made to the embodiments of the presently disclosed surgical systems and endoscopes. Therefore, the above description should not be construed as limiting, but merely as exemplifications of embodiments. Those skilled in the art will envision other modifications within the scope and spirit of the disclosure.

We claim:

1. An elevator cab comprising:
   an intake plenum formed in a ceiling of the elevator cab;
   a plurality of intake ducts formed in sidewalls of the elevator cab, the intake plenum and the plurality of intake ducts including a plurality of openings in fluid communication with an interior of the elevator cab, wherein the plurality of openings in the plurality of intake ducts are dispersed along the length of the plurality of intake ducts and the dispersion extends from the ceiling to approximately three feet above a floor of the elevator cab;
   a fan configured to draw elevator air from the elevator cab through the plurality of openings formed in the intake plenum and the plurality of openings formed in the plurality of intake ducts;
   a kill box, including a source of ultraviolet-C (UVC) light, and configured to receive air via the fan, wherein the source of the UVC light is configured to sterilize air removed from the elevator cab, the kill box including a first filter positioned between the fan and the source of UVC light, and a second filter positioned between the source of UVC light and an outlet of the kill box, wherein a flow of elevator air through the kill box is slowed by the second filter to prolong exposure of the elevator air to the source of UVC light such that pathogens in the elevator air are sterilized;
   an exhaust plenum in fluid communication with the outlet of the kill box;
   a plurality of exhaust ducts formed in a rear wall of the elevator cab and extending a length of the elevator cab; and
   a plurality of openings in the rear wall proximate a floor of the elevator cab, each of the plurality of openings in communication with one of the plurality of exhaust ducts and exhausting sterilized air from the kill box into the elevator cab.

2. The elevator cab of claim 1, wherein the fan, source of UVC light, and the first and second filters are configured to reduce volatile organic compounds in the elevator air by about 32% or more.

3. The elevator cab of claim 1, wherein the fan, source of UVC light, and the first and second filters are configured to reduce particles less than 10 microns in the elevator air by about 95%.

4. The elevator cab of claim 1, wherein the fan, source of UVC light, and the first and second filters are configured to reduce particles less than 2.5 microns in the elevator air by about 95%.

5. The elevator cab of claim 1, wherein the fan, source of UVC light, and the first and second filters are configured to reduce particles less than 1 micron in the elevator air by about 97%.

6. The elevator cab of claim 1, wherein the fan, source of UVC light, and the first and second filters are configured to reduce particles less than 0.3 microns in the elevator air by about 89%.

* * * * *